(12) United States Patent
Souluer

(10) Patent No.: US 6,868,171 B2
(45) Date of Patent: Mar. 15, 2005

(54) DYNAMIC COLOR IMAGING METHOD AND SYSTEM

(75) Inventor: Farid Souluer, Chester Springs, PA (US)

(73) Assignee: Ultratouch Corporation, Chapel Hill, NC (US)

( * ) Notice: Subject to any disclaimer, the term of this patent is extended or adjusted under 35 U.S.C. 154(b) by 0 days.

(21) Appl. No.: 10/398,322

(22) PCT Filed: Oct. 9, 2001

(86) PCT No.: PCT/US01/31514

§ 371 (c)(1),
(2), (4) Date: Nov. 24, 2003

(87) PCT Pub. No.: WO02/33649

PCT Pub. Date: Apr. 25, 2002

(65) Prior Publication Data

US 2004/0057608 A1 Mar. 25, 2004

Related U.S. Application Data

(63) Continuation-in-part of application No. 09/890,501, filed on Aug. 1, 2001, which is a continuation-in-part of application No. 08/957,648, filed on Oct. 24, 1997, now Pat. No. 6,192,143.
(60) Provisional application No. 60/238,350, filed on Oct. 6, 2000.

(51) Int. Cl.[7] .............................................. G06K 9/00
(52) U.S. Cl. ...................................................... 382/128
(58) Field of Search ................................ 382/128, 129, 382/130, 133, 162, 164, 165, 173, 182, 282, 283, 285; 600/312, 313, 314, 183; 378/37; 430/42, 44; 435/1.1, 40.5, 40.52; 424/10.3

(56) References Cited

U.S. PATENT DOCUMENTS

| 5,301,681 | A |   | 4/1994  | De Ban et al.         | 600/549 |
|-----------|---|---|---------|-----------------------|---------|
| 5,361,767 | A |   | 11/1994 | Yukov                 | 600/442 |
| 5,465,722 | A |   | 11/1995 | Fort et al.           | 600/447 |
| 5,568,811 | A |   | 10/1996 | Olstad                | 600/443 |
| 5,657,760 | A |   | 8/1997  | Ying et al.           | 600/439 |
| 5,749,364 | A |   | 5/1998  | Sliwa, Jr. et al.     | 600/438 |
| 5,882,330 | A | * | 3/1999  | Lemelson              | 604/503 |
| 6,015,384 | A |   | 1/2000  | Ramamurthy et al.     | 600/440 |
| 6,016,439 | A | * | 1/2000  | Acker                 | 600/411 |
| 6,031,930 | A |   | 2/2000  | Bacus et al.          | 382/133 |
| 6,055,452 | A |   | 4/2000  | Pearlman              | 600/547 |
| 6,099,471 | A |   | 8/2000  | Torp et al.           | 600/438 |
| 6,745,067 | B1| * | 6/2004  | Zavislan et al.       | 600/473 |
| 2003/0103665 | A1 | * | 6/2003 | Uppaluri et al.     | 382/131 |

* cited by examiner

Primary Examiner—Andrew W. Johns
Assistant Examiner—Shervin Nakhjavan
(74) Attorney, Agent, or Firm—Woodcock Washburn LLP

(57) ABSTRACT

The present invention provides color images of tissue characteristics for determining the existence can location of tissue anomalies. An image of tissue is received, divided into pre-determined portions and accompanied by X and Y coordinates describeing the tissue relative to a subject. Characteristic data of the tissue is received for each portion of the image and is displayed by color according to characteristic data value. Characteristic data can also be determined and displayed for each portion of the image over multiple levels. Multiple images, one for each level, can be scrolled through for a common set of X and Y coordinates of tissue. Or, a three dimensional image is created, having respective levels displayed simultaneously, with color representative of the tissue characteristics for the entire depth of the tissue investigated. Additionally, color images are developed that compare and display differences in characteristic data of tissue over time.

58 Claims, 10 Drawing Sheets

DYNAMIC COLOR IMAGING METHOD AND SYSTEM

RELATED APPLICATIONS

This application claims priority from pending U.S. Provisional Application Ser. No. 60/238,350, filed Oct. 6, 2000, entitled "A Dynamic Color Density Mapping System". This application is also a continuation-in-part of U.S. application Ser. No. 09/890,501, filed Aug. 1, 2001, which is the National Stage of International Application No. PCT/US00/02341, filed Jan. 29, 2000, which claims priority to U.S. application Ser. No. 09/241,193, filed Feb. 1, 1999, which is a continuation-in-part of U.S. application Ser. No. 08/957,648, filed Oct. 24, 1997, now U.S. Pat. No. 6,192,143.

FIELD OF THE INVENTION

This invention relates to a method and system for creating images of tissue characteristics, and more particularly to a method and system for creating dynamic color images of tissue density, the color images displaying variations of tissue density over selected regions to facilitate the accurate and early detection of tissue anomalies.

BACKGROUND OF THE INVENTION

The early detection of anomalous human tissue, and in particular the detection of undesirable tissue such as fat, fibrous tumors, or cancerous tissue is a much felt need. For example, recent findings indicate that one out of eight women will develop breast cancer, the second leading cause of death in women. The earliest indication of breast cancer generally is the occurrence of a painless lump, sometimes associated with nipple discharge and skin retraction. Unfortunately, later, more obvious and less survivable indications of cancer are generally due to metastases to bone, brain, lungs and liver. Accordingly, early detection of anomalus tissue and tissue changes is essential for improvement of survivability and effective treatment. Attempts at early detection through monthly self-examinations and mammography have proven beneficial but have not satisfied the need for more effective methods of early detection and corresponding treatment.

By way of example, if small lumps, less than 20 mm, can be detected early they can then be diagnosed by a biopsy and treated should the lump be found to be malignant. Accordingly, early detection allows for less invasive treatment, such as a lumpectomy with possible radiation treatment of axillary nodes making less likely the need for a modified radical mastectomy with axillary node dissection. In addition, through early treatment the five-year survival rate can be improved by as much as 85 percent. Absent early detection, distant metastasis can reduce survival rates to 10 percent or less. The present invention addresses this very critical need.

Although early detection is essential, it can be difficult to achieve even by skilled physicians. Monthly self-examinations are helpful, particularly when followed by the examination of a physician in the event a mass is self-detected. It is, however, difficult for an unskilled individual to do a thorough examination, and unlikely that very small lumps will be detected.

Presently, anomalies in tissue, particularly breast tissue, are detected mostly by periodic palpation by the hand of a physician or radiographic mammography. To be effective, however, hand palpation must be frequent, particularly in older women, to detect tumors before the tumors metastasize. Unfortunately, the subjective nature of hand palpation and the frequency required to make these examinations effective create limitations rendering hand palpation examinations ineffective due to inconvenience, availability, and cost In addition, mammography is troublesome due to the concern of accumulated radiation exposure from frequent mammograms. Furthermore, mammography, unlike palpation, can be limited because very small tumors are not detected, particularly in the denser breast tissue of younger women.

In addition to anomalies, it is also important that changes in tissue structure, and changes in tissue characteristics, be detected and monitored over time. The problem, therefore, is how to detect minor changes in tissue. For example, hand palpation of tissue may not reveal small characteristic changes or anomalies within breast tissue until the changes are so substantial, or the anomalies so prominent, that they are no longer responsive to early treatment.

Another problem limiting the effectiveness of hand palpation is the inability to record, retain, and at a later time recall, historical data of prior detected anomalies, including location and the nature of the changes over time. This is particularly the case for soft anomalous tissue located further from the surface of the skin, having diameters less than 10 mm. Also, anomalies deeper in the tissue of large breasts are particularly difficult to detect by hand palpation. Even if detected, it is often not possible to characterize the tissue or changes in the tissue due to the subjective nature and lack of standards for hand palpation, which almost entirely depends on the skill and sensitivity of the examining physician.

Accordingly, the present invention addresses each of the aforementioned problems and urgent needs. The present invention provides methods and systems for early detection of tissue anomalies and changes in tissue characteristics through color imaging of tissue characteristics, the color images displaying variations of predetermined tissue characteristics over selected regions of tissue to facilitate the accurate and early detection of tissue anomalies, even very small anomalies. The present invention also addresses the need to objectively determine tissue characteristics and produce, maintain, and compare images of these characteristics, over time, the images mapping selected regions of tissue to track characteristic changes over time.

SUMMARY OF THE INVENTION

The present invention is a method and system for developing color images of tissue characteristics, the color images displaying variations of pre-determined tissue characteristics over selected regions of tissue to facilitate the accurate and early detection of tissue anomalies.

In one aspect of the invention, a method and system develops images displaying characteristics of tissue by first developing an image of the tissue. The image is divided into pre-determined portions and is accompanied by data describing a first and a second coordinate of the tissue relative to a subject body for each portion of the image. The system receives characteristic data of the tissue for each portion of the image, then associating a color to the characteristic data for each portion of the image. The color associated to the characteristic data is based upon the value of the characteristic data, so that the color displayed, for each portion of the image, portrays the degree of variation of the value of the characteristic data relative to that for other portions of the tissue investigated. The system then displays the color for each portion of the image.

In one aspect of the invention, the data describing the first and the second coordinate of the tissue relative to the subject body is received from a camera. The characteristic data can be received from a palpation device (i.e., a detection head having one or more palpation probes). A location head may provide positional data associating the characteristic data detected by the palpation device with that portion of the image displaying that coordinate of the tissue detected.

In another aspect of the invention, the system further calculates and records a size of tissue for any predetermined characteristic value. The characteristic data may relate to one property, or may relate to a combination of properties. Examples properties are tissue density, temperature, color, resistance, conductivity, impedance, ultrasound and sampling information. Further properties may include a distance traveled by a palpation probe, a velocity of travel of the palpation probe and a time of palpation at each probe contact point with tissue.

In another aspect of the invention, when the characteristic data incorporates multiple properties, the system carries out an intermediate step of associating code to the multiple properties of characteristic data before color is assigned. First, a set of codes is assigned to each property incorporated into the characteristic data. A specific code within the set is assigned for each property based upon the value detected for that property for each portion of the image. A resultant code is calculated for each portion of the image based on a formula that considers each of the included properties and the specific code assigned for that property. Then, a color is associated to the resultant code.

In another aspect of the invention, characteristic data of tissue is received for each portion of the image for each of a plurality of third coordinate values related to that portion of the image. The system processes and displays multiple image layers, each image layer corresponding to similar first and second coordinates of the tissue relative to the subject body. Each image layer can be scrolled through to provide incremental views of depth for any given coordinate.

In another aspect of the invention, the multiple image layers are displayed simultaneously, one over another, to create a virtual, three-dimensional image. The color displayed for each portion of the three-dimensional image is selected based on a formula that considers the characteristic data of the tissue for each layer simultaneously displayed for that portion.

In another aspect of the invention, the system processes recorded information related to characteristic data determined for selected first, second and third coordinates of tissue and programmably compares the data with previously determined data related to the same coordinates of the same tissue. The system displays an image of the respective tissue, and color is assigned to each portion of the image based upon any change, and degree thereof, in the characteristic data for that portion of the image. The change displayed could be directed to a difference, in absolute value, of the characteristic data compared for each portion of the image, or the change displayed could be a first derivative analysis of the characteristic data compared, or the change displayed could be a combination thereof.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
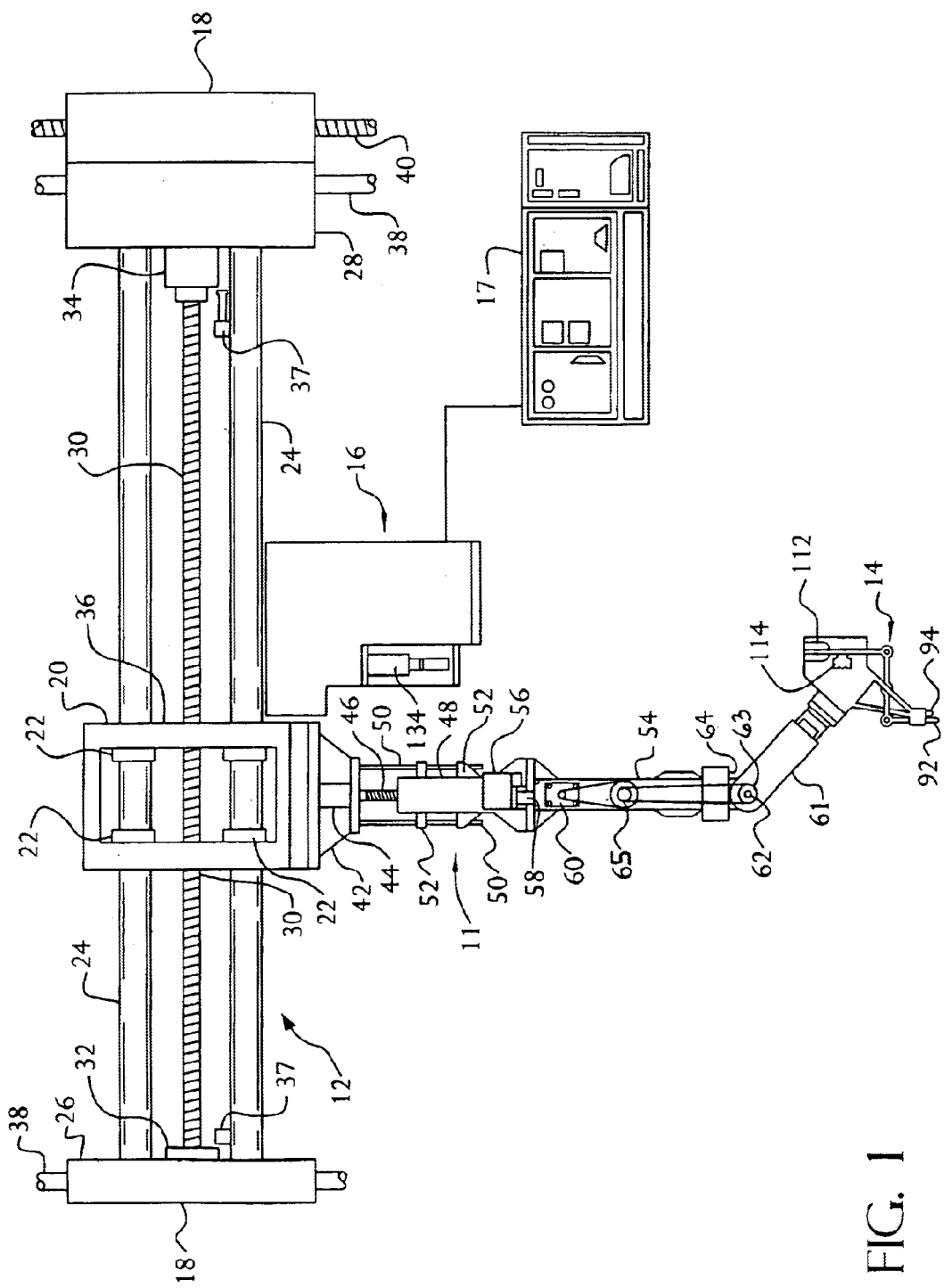
FIG. 1 is an illustration of a detection device for detecting anomalies in human tissue according to the present invention.

Referring now to the drawings, wherein like numerals indicate like elements, there is shown in FIG. 1 an illustration of one embodiment of an apparatus 10 for detecting anomalies in human tissue. In one aspect of the invention, the apparatus 10 includes a carriage (also referred to as a robot arm) 11 that is mounted at a proximal end to a horizontal support 12 for movement therealong, and a detector 14 (also referred to as a detection head) that is mounted at the distal end of the carriage 11. The detector is shown in more detail in FIGS. 3 and 4 and is used to detect the characteristics of tissue by palpation. A locator 16, for locating the position of a patient relative to some reference, is mounted to the carriage 11 for movement therewith. Data is produced by the palpation device and collected, stored and displayed in a manner that will capture details of the detected anomalies for comparison with historical data The invention provides data about the tissue under investigation by means of an automated biopsy and treatment by means of surgical attachments for the delivery of radiologic, chemotherapeutic, or laproscopic surgery.

For example, the digital information can be received, stored, processed or displayed in a similar manner to existing medical devices such as a CAT scan or MRI. The present invention also produces multi-dimensional images viewed on conventional computer monitors. Images are produced using color to indicate areas of differing tissue density. These images are further enhanced by combining tissue density information with tissue color and temperature information to detect and track small tumors in discrete tissue areas.

Horizontal Movement

Figure 6:
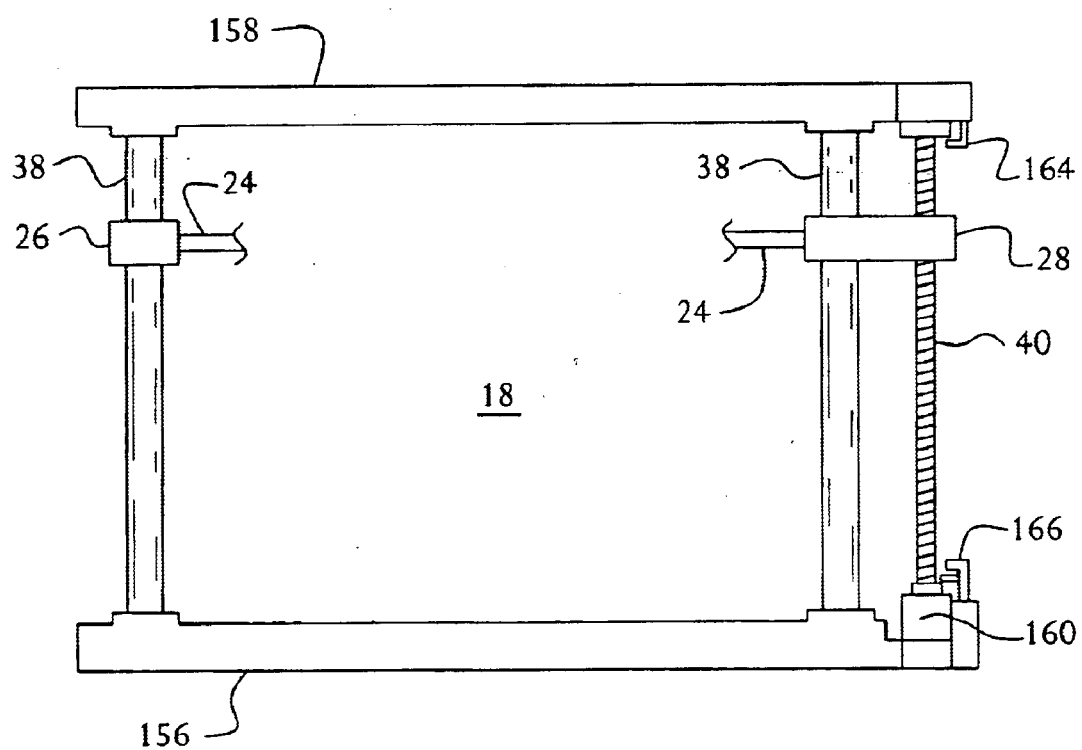
FIG. 6 is an illustration of a vertical positioning mechanism for use with a detection device.

In one embodiment of the invention, the support structure of which is detailed in FIG. 6, the detector 14 is positioned over the patient and provided with horizontal movement by a horizontal support 12 that is mounted on a vertical support mechanism 18, allowing the horizontal support 12 to move in a vertical direction. The horizontal support 12 includes a traveler 20 that rides on bearings 22 along rods or tubes 24 that are secured at their ends to end blocks 26, 28. A lead screw 30 is driven by a drive motor 34 and extends between a pair of end blocks 26, 28 and bearings 32. Lead screw 30 extends through correspondingly threaded openings 36 of the traveler 20 so that the traveler 20 will move to the right or left as the lead screw 30 is rotated in one direction or the other, and limit switches 37 are used to prevent over travel of the traveler 20. Guide rods 38 extend vertically through the end blocks 26, 28 so that the horizontal support 12 can be moved vertically by means of a lead screw 40 that extends vertically through one end block 28.

The carriage 11 includes a base 42 secured to the traveler 20. A motor 44 within the base 42 rotates a screw 46 that is threaded into an intermediate body 48 to raise and lower the intermediate body 48 as the screw 46 is rotated one way or the other. A pair of guide rods 50 extend through a bracket 52 to guide movement of the intermediate body 48. A lower body 54 is secured to the intermediate body 48 for rotation relative thereto. A motor 56 is mounted on the intermediate body 48 with the lower body 54 mounted on the motor shaft 58 for rotation with the shaft 58.

Vertical Movement

The detector 14 is positioned over the patient and provided with vertical movement by a mechanism for raising and lowering the entire carriage 11, as shown in FIG. 6. The carriage 11 is supported by a pair of vertical guide rods 38 that extend from a sturdy base 156 to a top plate 158. A pair of end blocks 26, 28 support the horizontal support 12 and provide vertical movement therealong.

A motor 160 rotates a sturdy lead screw 40 threaded through a block 28. An upper limit switch 164 and a lower limit switch 166 prevent movement of the horizontal support 12 beyond desired limits. For a very strong, sturdy assembly, the base 156 will rest on the floor or a sub-floor so that the platform 67 could be positioned within the frame formed by the base 156, the top plate 158 and the guide rods 38.

Positioning Arm

An arm 61 is pivotally mounted at a pivot 62 on a bracket 64 that is mounted on the distal end of the lower body 54. A motor 60 on the lower body 54 drives a pulley 63 on the arm 61 through a jackshaft 65. Thus, the entire carriage 11 can be moved horizontally by the horizontal support 12, and vertically by the vertical support 18. The lower body 54 of the carriage 11 can be rotated 360°. The arm 61 carries the detector 14 which can be pivoted through at least 120°. The arm 61 can also carry and operate other devices such as, but not limited to, attachments for the delivery of acoustic, radiologic, chemotherapeutic treatments or laparoscopic surgery. The combination of movements just described permit the detector 14 to be positioned in any desired location relative to any portion the surface of human body, particularly a breast.

Although a particular positioning arrangement of the detector 14 has been described, it is understood that the invention can include any type of positioning system that will provide several degrees of freedom of movement for the detector 14 or other devices.

Position and Location System

Figure 2:
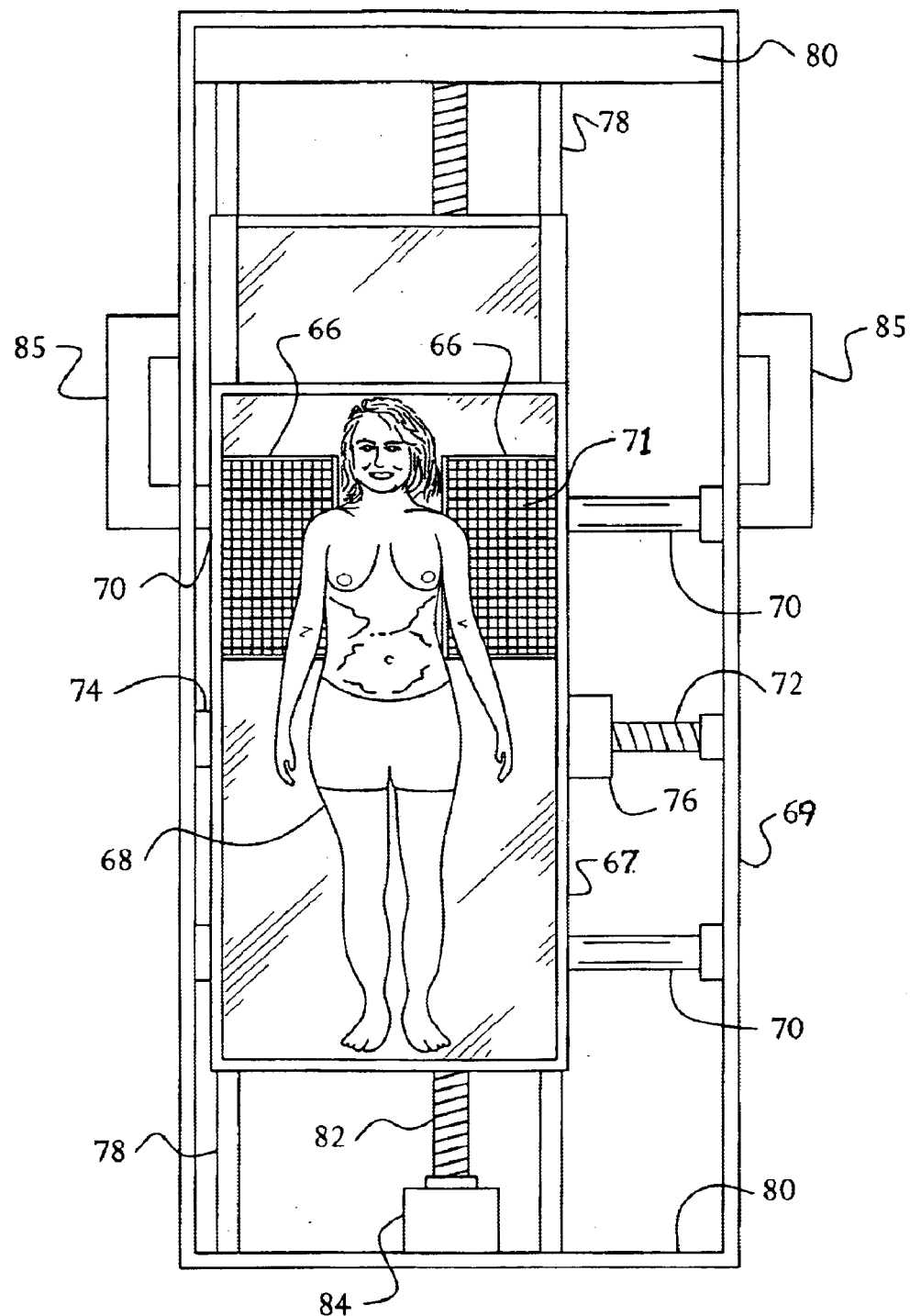
FIG. 2 is an illustration of a patient positioning platform for use with the detection device shown in FIG. 1.

In one embodiment of the invention, an investigation of a selected body part or region is started by positioning the patient on a platform (also referred to as a bed) 67 that is affixed to a position adjusting assembly 69, such as that shown in FIG. 2. The platform 67 is typically positioned below the detector 14 of FIG. 1. The platform 67 has a comfortably padded upper surface and a matrix board 66 with a location pattern 71, that is typically positioned adjacent to the shoulders of the patient 68.

The matrix board 66 and pattern 71 are used to maintain registration between the specific points of the patient's body under investigation and the acquired measured data. In addition, the matrix board 66 and pattern 71 are used to maintain registration between subsequent measurements taken at different times for the same patient 68.

For example, optical measuring means such as, but not limited to, a video camera, a fiducial reference target, or a laser location device can be used to locate the exact position of the patient or selected body parts such as arms, shoulders and neck relative to the matrix board 66 and its pattern 71 during an investigation.

In subsequent investigations, the patient 68 is positioned on the platform 67, the optical system, with or without the aid of adaptive software techniques, will correlate prior and presently collected location data and measurement data. Further, movement by the patient 68 that may introduce errors in the measured data can be corrected during the investigation by error correction techniques provided by the optical system. Although it is desirable that the patient 68 be placed in the same position for each investigation, it is not required since that the invention can correct for any change in position by means of position reference data collected during each periodic investigation.

Referring to FIG. 2, the underside of platform 67 includes conventional tubular bearings through which a pair of horizontal guide rods 70 pass. A central threaded rod 72, driven by a motor 76, engages end bearings 74. As the motor 76 rotates, the platform 67 is moved right to left. The platform 67 is similarly moved up and down by means of a pair of guide rods 78 secured to end walls 80 of assembly 69 and driven by a motor 84 that rotates a threaded rod 82 which moves the platform 67 as desired.

The invention provides a means to control the position of the patient for consistent reinvestigation. This is accomplished by means of the platform 67 and a locator (also referred to as a location device, sensor, or head) 16, shown in FIG. 5. The locator 16 provides accurate location information for positioning the patient 68 on the platform 67 or for correlating the data with subsequent or prior measurements by means of geometric translation which can be achieved by pattern recognition or reference to a fixed fiducial reference.

Figure 5:
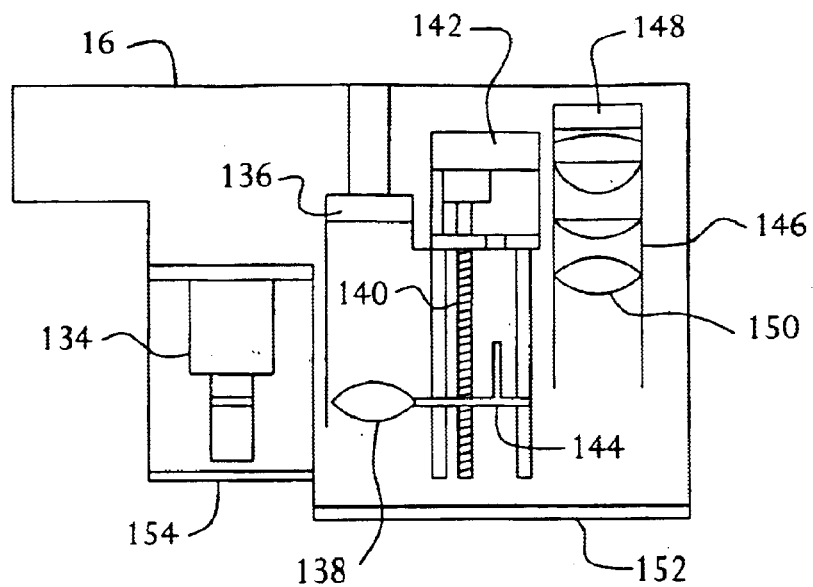
FIG. 5 is an illustration of a locator head assembly according to the present invention.

For example, a digital camera 134 is used to produce a digitized image of the tissue under investigation. The image is then compared by a computer system or technician to prior or subsequent images. A white light source 136 can be used to produce a three-dimensional image. As shown in FIG. 5, the light source 136 is employed with an auto-focus system having a lens 138, and a lead screw 140 rotatable by a motor 142 and threaded through a lens mount bracket 144 for focusing a light spot on the surface of the tissue under investigation. The spot of light is moved transversely and focused at different depths along the tissue surface. Data of the focus position of the 6lens 138 is collected and used to produce a three-dimensional image of the tissue surface.

In another aspect of the invention, as shown in FIG. 5, a laser scanner 146 may be used to create a three-dimensional image. The laser scanner 146 includes a laser emitter 148 and a focusing system 150 for producing a focused laser spot on the surface of the tissue under investigation. For example, a laser operable in the range of 680–820 nm with a power level about 0.0095 should provide sufficient laser power to produce an image without damaging the tissue under investigation.

In all aspects of the invention, prior and subsequently collected image data can be used to translate position data of the tissue under investigation. This feature provides enhanced capabilities in the examination of anomalies in the tissue under investigation. For example, a three-dimensional image can be divided into a matrix of cubes or slices with geometric indicia (e.g., a cube might be identified as cube 2, 4, 9 on an x-y-z axis basis) and locations can be directly compared between the light spot image and the probe palpation locations.

Palpation Systems

Figure 3:
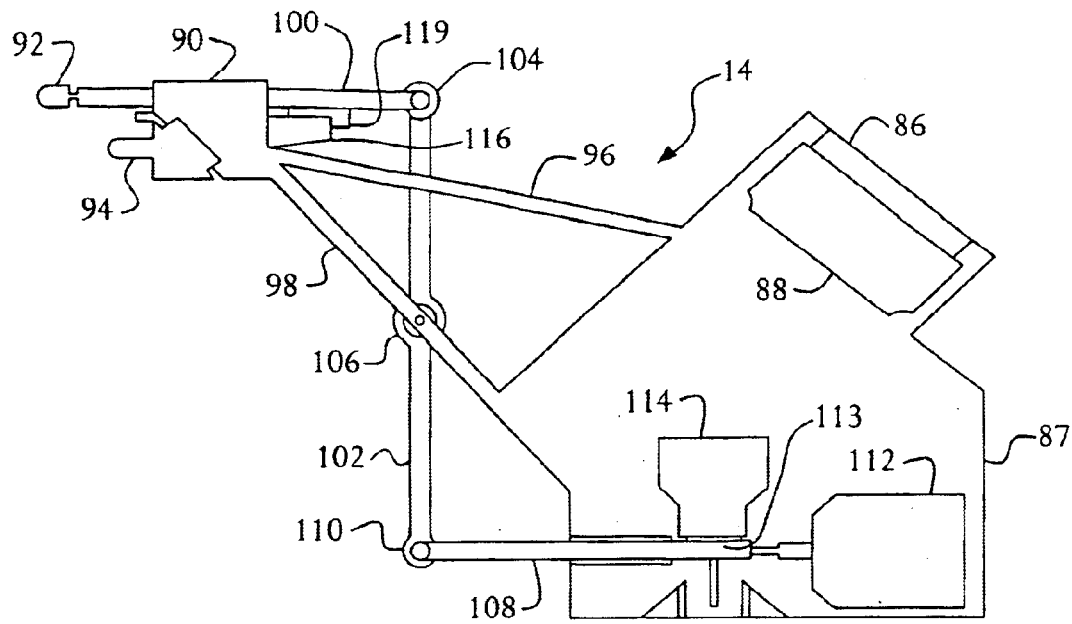
FIG. 3 is an illustration of a detection head and actuator according to the present invention.

One embodiment of the detector 14, according to the present invention, is shown in FIG. 3. The detector 14 is shown with a removable connection 86 for attachment onto a rotatable arm 61. The detector 14 has a palpation probe housing 90 for supporting a palpation probe or finger 92 and a sensor 94. The sensor 94 includes, but is not limited to, a device for sensing distance, acoustic waves, x-rays, MRI, color, and temperature. The sensor 94 may also be mounted to the detector's main housing 87. The palpation probe 92 is designed to simulate a physician's finger during a palpation investigation like that in a manual breast examination. In a preferred embodiment, the palpation probe 92 is composed of a disposable material, such as, but not limited to, glass or plastic.

Distance is measured by means of a sensor 94, which is an autofocus system like that used in cameras. The autofocus system can provide precise data such as the distance between the breast surface and a known reference point within the sensor. In another aspect of the invention, a plurality of spaced range finders can be used to measure the angle with respect to the breast surface so that the orientation of the palpation probe 92 is maintained at a pre-determined angle such as, but not limited to a, perpendicular to the tissue under investigation.

Color is sensed by a color sensing device such as a photo-detection diode or spectrum detection sensor. In addition, a prism or diffraction grating for dispersing incoming light and refracting each color of light to an independent photoelectric sensor may also be used.

Referring to FIG. 3, in one aspect of the invention the palpation probe 92 is secured to the distal end of a first shaft 100 which is slidably connected to the housing 90 and pivoted, at its proximal end, to the distal end of a first arm 102 at a pivot point 104. The first arm 102 is rotatable about an axis 106 that is centrally located along a second arm 98. The proximal end of the first arm 102 is pivotally connected to a drive shaft 100 at a second pivot point 110. When the drive shaft 108 is moved axially by an actuator located within an actuator housing 112, which is shown in detail in FIG. 4, the first shaft 100 and the palpation probe 92 move a proportional distance in the opposite direction.

The motion of the palpation probe 92 is then measured to determine time, distance traveled, velocity, and resistance encountered by the probe 92 as it comes in contact with the tissue under investigation. For example, an optical reading device 126 having a laser source is located in a reader housing 114 for detecting movement of the palpation probe 92 by means of an optical encoded gradient 113 attached to the drive shaft 108. The parameters of time, distance traveled, and rate thereof, are used to determine a characteristic value of the tissue under investigation in response to the feedback resistance experienced by the palpation probe 92 when it is pressed against the tissue under investigation.

To further improve the accuracy of the measurements, a position error correction sensor 116 is used in cooperation with a position detection member 119 such as, but not limited to, an optical gradient, inertial displacement device or motion sensor, that is attached to the first shaft 100 to detect and correct positioning errors. The position error correction sensor 116 is used to correct movement and position errors of the components of the detector 14. Movement of the palpation probe is accomplished by the activation of magnetic coils 118, which are detailed in FIG. 4. Slight changes in position of the tissue under investigation, like that caused by breathing, can be sensed by the palpation probe and a corresponding position correction signal can be sent to selected coils of the magnetic coils 118 to correct displacement errors.

In one embodiment of the invention, the palpation probe 92 is moved by a series of electromagnetic coils 118 that are arranged in a uniformly spaced relationship along a central tube 120. In a preferred configuration, the electromagnetic coils 118 may be formed as a continuous helix to form a solenoid. An end shaft 122 is axially secured to the proximal end of the drive shaft 108 and extends into a tube 120.

An end shaft 122 is formed from a magnetic material so that when the coils 118 are actuated sequentially, beginning with the coil adjacent to the end shaft 122, the magnetic forces in the coils 118 will pull the end shaft 122 into the tube 120. Alternately, the coils 118 are actuated individually in a sequence or by applying incrementally increasing voltages to the coils 118. The extension of the drive shaft 108 is controlled by the movement of the end shaft 122 which can be adjusted by a threaded mechanism 128. The maximum excursion of the drive shaft 108 is limited by a pin 130 extending from the drive shaft 108 and a pair of limit switches 132.

The magnetic force applied is sufficient to advance the palpation probe 92 to compress the tissue under investigation but not enough to cause discomfort or damage to the tissue. The time and distance the probe advances will be in proportion to the density of the tissue, resulting in less time and movement for dense tissue and more time and movement for less dense tissue.

In operation, a first coil 118 is actuated to move the palpation probe 92 a predetermined force, distance, time, or some combination thereof. The first coil 118 is energized in a step-wise fashion at about 250 mv increments from 0 to 10 volts, and the change in force is about 10 grams per $mm^2$ per step. When the probe fails to move a predetermined distance for a predetermined time, additional force is applied by means of a second coil 118. It is to be understood that additional coils similarly operated, can be added as required.

The resistance characteristic of the tissue under investigation is determined when the applied pressure, distance traveled or time of pressure reaches a predetermined value. The parameters of force, distance or time are measured at the predetermined value and the parameter information is then transferred to information storage means and/or to a controller for processing, analysis, and the production of multidimensional images.

In one aspect of the invention, the palpation information including, but not limited to, distance, force, time, resistance, and characteristic value of the tissue under investigation, are obtained by encoding and transmitting the acquired palpation information. As shown in FIG. 4, a laser optic card 124 associated with the shaft 108 is read by a laser card reader 126 which transmits the encoded information to a storage device or the controller 17 for processing. The controller then processes the information as required for use by other devices or in a manner similar to CAT systems or equivalent devices.

Figure 4A:
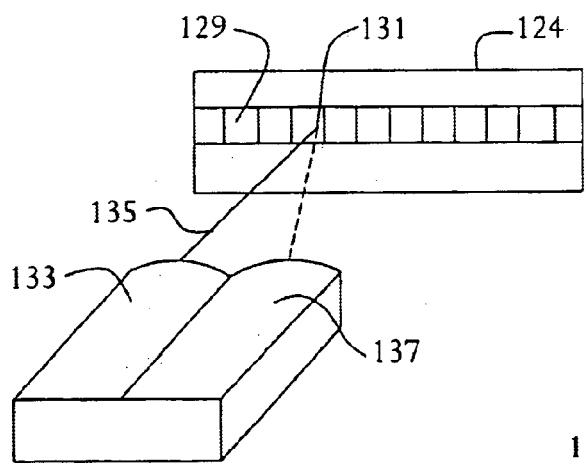
FIGS. 4 and 4a illustrate a position and movement measurement device used with the detection head and actuator shown in FIG. 3.
Figure 4:
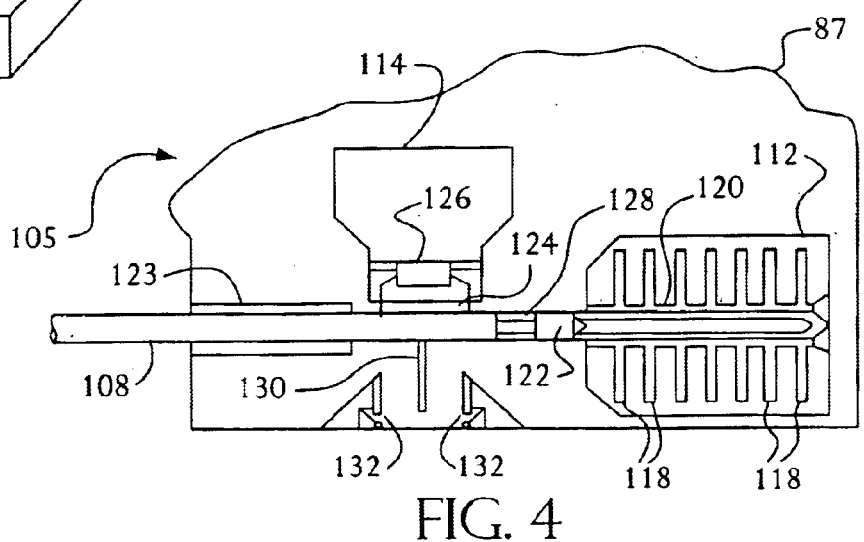

An example of a laser card 124 that is to be used with the laser card reader 126 is shown in FIG. 4a. The card 124 has a series of reflecting areas 129 that are separated by non-reflective areas 131. The non-reflecting areas 131 of the card 124 can be light absorbing or transparent. A laser transmitter 133 directs a laser beam 135 against the patterned area of the laser card 124. When the laser beam 135 hits a reflecting area, reflected light is picked up by a receiver 137. As the card 124 is moved in a direction transverse to the reader 126, the pattern of reflected pulses are counted to measure movement of the drive shaft 108 and the palpation probe 92. The reflecting areas can be as small as about 0.001 mm for more precise measurements of the motion of the palpation probe 92. Although only laser illumination has been discussed, it is to be understood that any form of illumination can be applied including, but not limited to, visible, infrared, or ultraviolet light, which may, or may not, be coherent, focused, columnated or diffused.

Palpation Actuators and Probes

Figure 7:
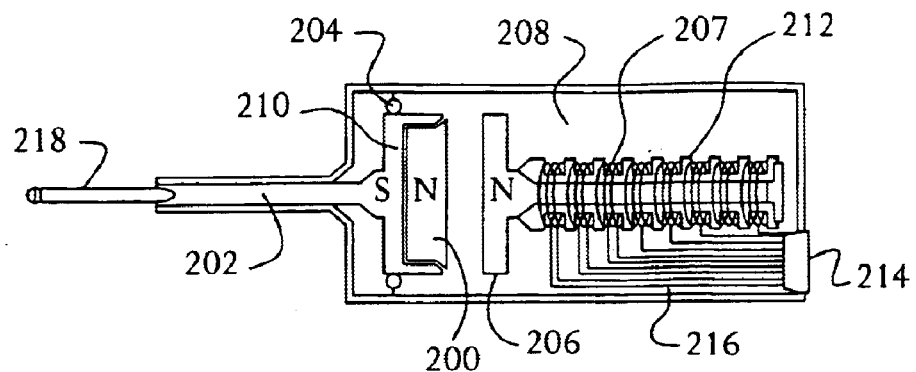
FIGS. 7 through 10 illustrate alternate embodiments of a detection head according to the present invention.

In another aspect of the invention, a palpation detector for detecting changes in density of tissue is shown in FIG. 7. A permanent magnet 200 is mounted on a non-magnetic rod 202 that is movable along the axis of the rod centerline. Suitable guides 204 such as rollers, ball bearings, a sleeve or the like are provided for smooth, low resistance, axial movement of the rod 202. The permanent magnet 200 is proximate to an electromagnetic coil head 206 mounted on a shaft 207 and fixed to a housing 208. The permanent magnet 200 and the electromagnet head 206 have common poles while the rod 202 has an opposing pole 210. Electromagnet head 206 is powered by any suitable number of powered coils 212 that are connected at a terminal 214 to a power source by supply wires 216. The magnets 200, 206 having common poles will oppose each other pushing the magnets 200, 206 apart when the electromagnet coils 212 are activated. The intensity of the opposing force is adjusted by the number of coils 212 and the level of power applied thereto.

Figure 11:
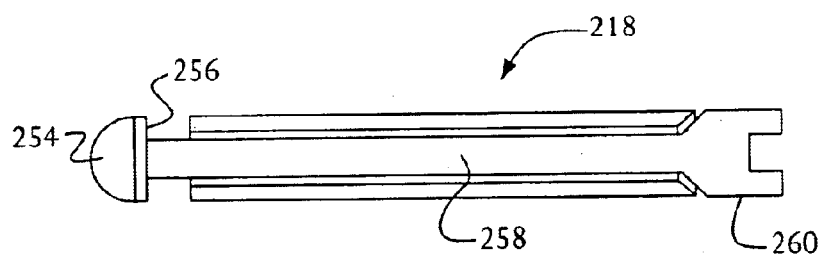
FIG. 11 illustrates a palpation tip for a detection head according to the present invention.

A palpation probe tip 218 is shown in FIG. 11, according to the present invention The palpation probe tip 218 is mounted on the distal end of the rod 202 which is brought into contact with (or to a predetermined distance from) the tissue under investigation, such as a breast surface by the carriage 11. The coil 212 is energized to increase the field around a shaft 207 to increase the field at the electromagnetic head 206 in order to force the permanent magnet 200 further away from the electromagnetic head 206, which moves the palpation probe tip 218 against the tissue. The tissue is depressed at the point of contact which transfers the tissue's elasticity characteristic in the form of a back pressure through the probe tip 218 and rod 202 toward the coil head 206.

The amount of back pressure applied including variations thereof are measured by recording instrumentation associated with the processor 17. It is to be understood that this pressure measurement system can be incorporated with any palpation device disclosed herein. Additional embodiments of palpation detection and actuator devices are shown in FIGS. 8–14.

Figure 8:
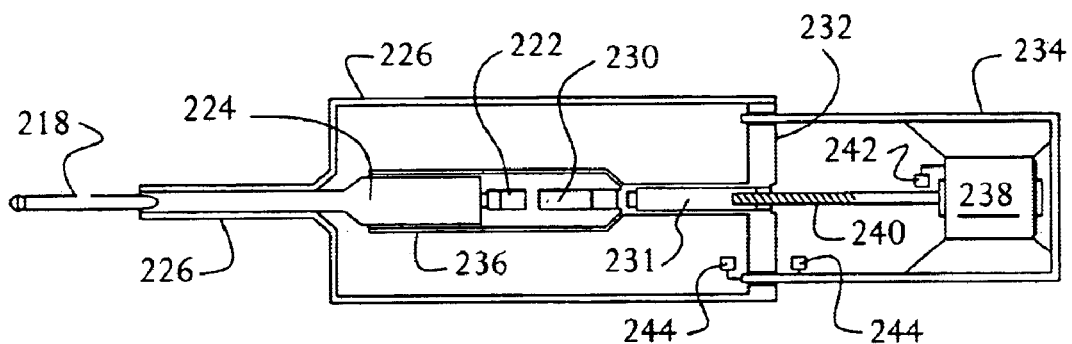

The detection and actuator device shown in FIG. 8 includes a permanent magnet 222 that is mounted at one end to an actuator rod 224 which is supported by a slidable sleeve 226 that is mounted on a housing 228. A tip 218 of the sort shown in FIG. 11 is secured to the other end of rod 224. A second permanent magnet 230 is mounted on a holder 231 that is coaxial with the rod 224. The permanent magnets 222, 230 are selected with common poles (north to north or south to south.) The holder 231 is supported on a disk 232 that is slidable within the housing 234 and coaxial with the rod 224. A sleeve 236 is preferably mounted on the holder 231 to aid in guiding the movement of the rod 224.

FIG. 11 shows a preferred embodiment of a palpation tip configuration 218. The tip configuration 218 includes a rounded endpiece 254 for contact with the tissue under investigation. Any suitable material may be used that can be inexpensively cleaned and made safely disposable is preferred. An end isolator 256, made up of an electrically insulating material is used to prevent static electricity discharge of the tissue. A core member 258 connects the endpiece 254 to a base 260 which is secured in any suitable manner, such as threads, to the rod 224.

In operation, the detector 14 is moved as discussed above to bring the palpation tip 218 into proximity with a selected location along the tissue under investigation. When the palpation tip 218 is initially brought into proximity to the breast surface, gravity causes the rod 224 and the permanent magnets 222 to move apart. A motor 238 mounted in a housing 234 drives a lead screw 240 which is threaded through a corresponding female thread 241 in a disk 232. The motor 238 may be any suitable motor, such as a low rpm DC motor or a stepper motor. Rotation of the lead screw 240 will move magnet 230 towards magnet 222 decreasing the intermagnet gap until the tissue resistance returns the intermagnet gap to a predetermined distance. The displacement of the holder 231 and the disk 232 is related to the tissue density characteristics of the tissue at the contact point. A sensor 242 counts the revolutions of the motor 238 to measure the corresponding degree of movement of the palpation tip 218 into the tissue.

Conventional safety sensors 244 may be provided to limit maximum movement of disk 232 (and movement of tip 218 in accordance with disk position) to prevent damage to the breast As mentioned above, the magnetic field between the magnets 222, 230 will act as a resilient mount for the palpation probe tip 218, limiting any damage or injury should the tip strike a breast or other surface.

Figure 9:
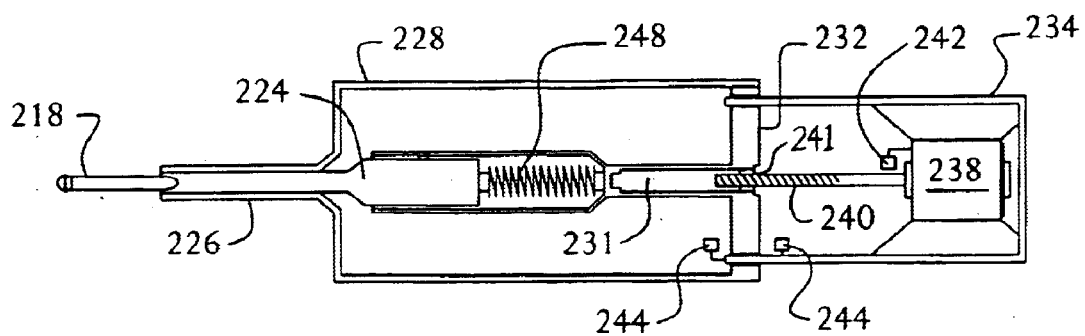

FIG. 9 shows another embodiment of a detector 14 having a pair of housings 228, 234, an actuator rod 224, sleeves 226, 236, a palpation tip 218, a holder 231, a disk 232, a motor 238, and sensors 242, 244. Instead of spaced permanent magnets 222, 230 a spring 248 is fastened between the proximal end of the rod 224 and the holder 231. The spring 248 is selected to provide a bias to the two juxtaposed ends of the rod 224 and the holder 231 to a particular, predetermined spacing. When the detector 14 is positioned over the tissue the palpation tip 218 extends downwardly under the force of gravity. The motor 238 rotates to move the disk 232 and holder 231 toward the rod 224 until the gap between the distal end of the holder 231 and the proximal end of the rod 224 is at the original predetermined distance. The total movement of the holder 231 is indicated by the number of revolutions of the lead screw 240 as measured by the counting sensor 242, which is indicative of the desired tissue characteristic.

Figure 10:
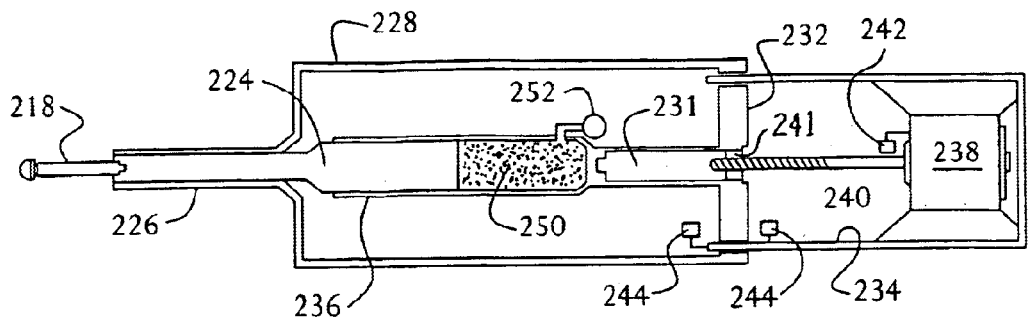

Another aspect of a detector 14 is shown in FIG. 10 having a gas 250 interface that is enclosed within a sleeve 236 at the proximal end of a rod 224. The sleeve 236 fits over the rod 224 in a sealing arrangement to prevent the pressurized gas 250 from escaping. Any suitable conventional seals may be used between the rod 224 and the sleeve 236.

The axial force applied to the rod 224 will change the gas pressure within the sleeve 236 which will be measured by a pressure sensor. When placed in contact with the tissue under investigation, the contact pressure is sensed 252 by the amount of pressure applied to the gas by the palpation probe 218. Pressure in the sleeve is adjusted by the rotation of the motor 238 which is counted by sensor 242. The amount of pressure applied by the rotation of the motor 238 is proportional to the desired tissue characteristic such as hardness and density.

Figure 12:
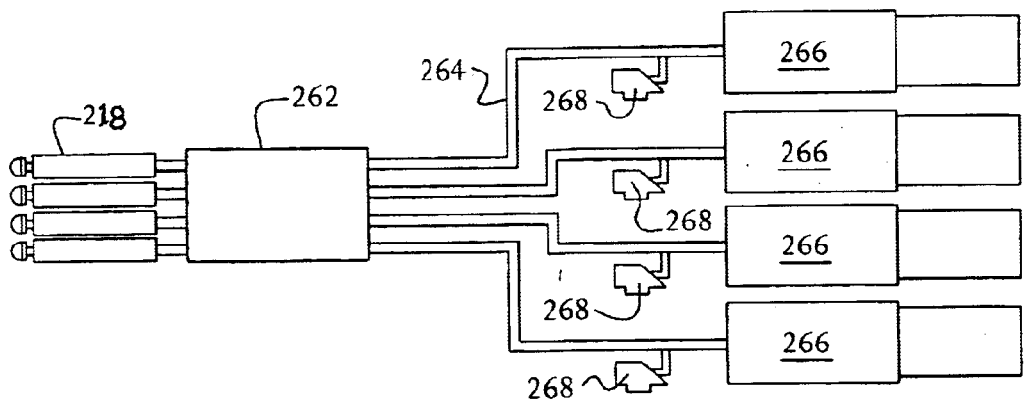
FIG. 12 illustrates a detection head having a plurality of parallel palpation tips according to the present invention.

FIG. 12 shows another detector 14 having a plurality of palpation probe tips 218 that are arranged in a parallel array and mounted on a corresponding number of actuator rods 262 for axial movement. In one aspect of the detector 14, a plurality of offset extension connectors 264 made of inflexible cables are used to transmit motion by means of transducers 266 that are connected to the output ends of the rods 262. An optical encoder and reader system 268 is incorporated to measure the movement of each palpation tip 218 during palpation of the tissue under investigation.

Figure 13A:
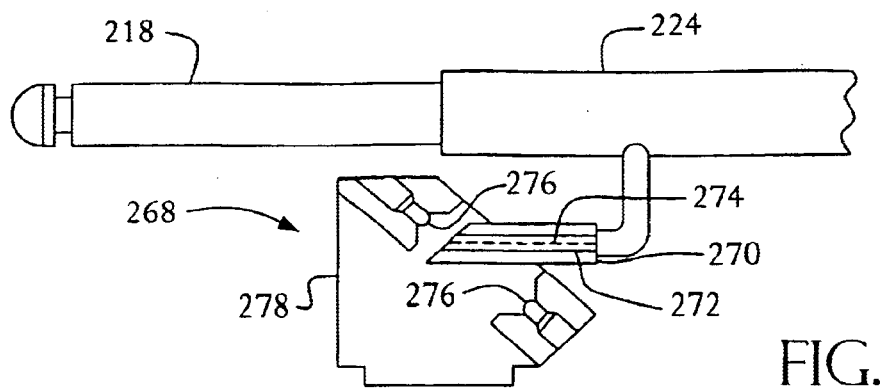
FIGS. 13a and 13b illustrate an actuator with an encoder according to the present invention.
Figure 13B:
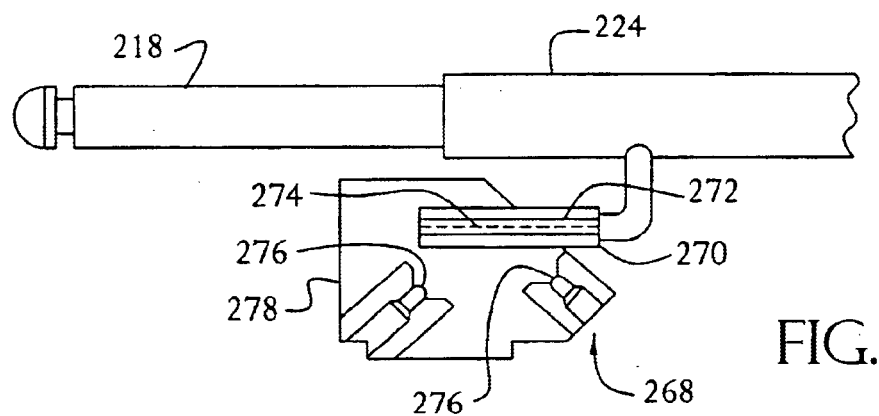

FIGS. 13a and 13b show two embodiments of the encoder and reader system 268 having a plurality of detectors 276 and encoder cards (strips) 272. The encoder system 268 includes an encoder slide 270 that is secured to the rod 224. The encoder slide 270 is secured to any suitable part of the rod 224 or to the palpation tip 218, as desired. The encoder slide 270 is transparent and includes a strip 272 with reflective dots 274 (or, in the alternative transparent dots in an otherwise opaque strip 272).

Decoder sensors 276 mounted on a housing 278 are provided on opposite sides of the encoder slide 270 and secured to the housing 278 by any suitable mounting means. The decoder sensors 276 are optical or laser sensors having light emitters of the sort used to read compact disks. The dots 274 are reflective particularly against a transparent background which causes light to pass between the pair of light transmitting decoder sensors 276. As the encoder slide 270 is moved, light from the emitters is either reflected by the reflective dots 274 or transmitted through the disk and onto the opposite sensor 276.

Figure 14:
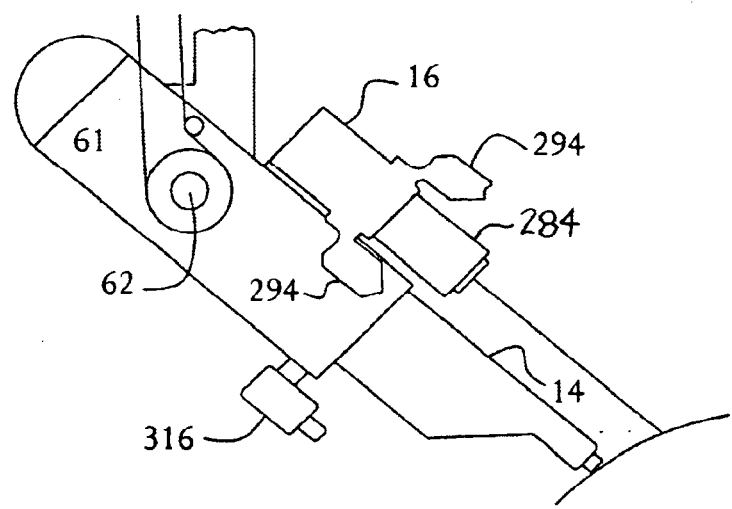
FIG. 14 illustrates an optical locating head and detection head mounted to a carriage according to the present invention.

Accordingly, the detected light indicates movement of the slide and the number of pulses of light received which are used to measure the distance of movement of the rod 224 and the palpation tip 218. Alternatively, when the dots 274 are transparent against an opaque background, light pulses received at the detector decoder sensor 276 will indicate the distance of movement of the rod 224 and the palpation tip 218. FIG. 14 shows another embodiment of the detector 14 in which the optical locating head 16 and detector 14 are both mounted at the end of the arm 61 on carriage 11.

Figure 15:
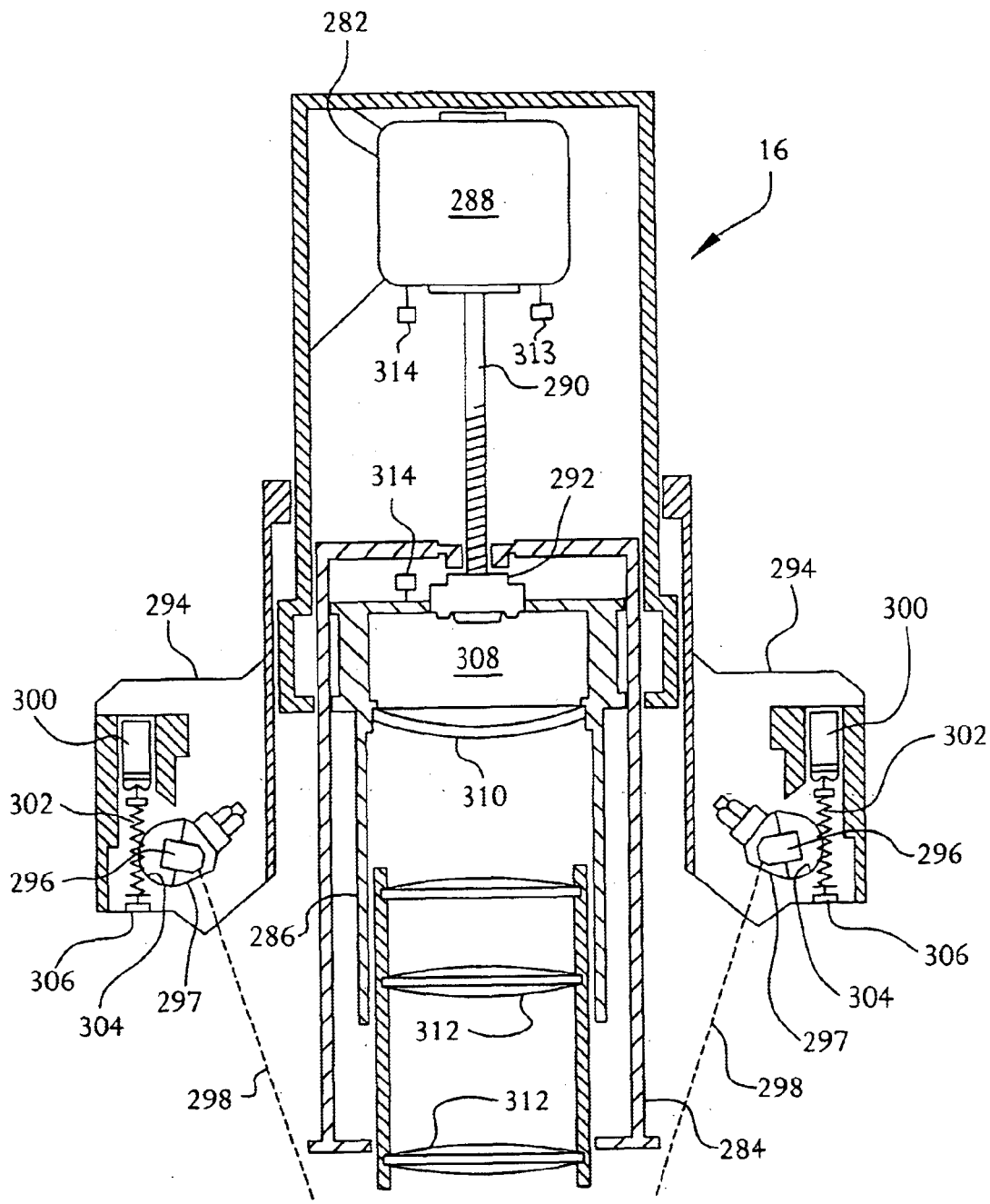
FIG. 15 illustrates the internal components of an alternate embodiment of a locator head assembly according to the present invention.

FIG. 15 shows and optical locator 16 having a motor housing 282 in combination with a detector 16. A lens enclosure 284 is secured to the motor housing 282 after precise positioning during manufacture of the assembly. A lens assembly 286 is slidably mounted within lens enclosure 284 for axial movement relative thereto. A motor 288 is mounted within the motor housing 282 and drives a lead screw 290 which is threaded through a nut 292 secured to lens assembly 286 to move the lens assembly 286 axially within lens enclosure 284.

Two laser beam positioning enclosures 294 are mounted on opposite sides of motor housing 282. Each enclosure 294 contains a pre-focused conventional (typically 680 to 850 nanometer) laser diode and light sensor 296. A prism 297 refracts light from a laser diode of the light sensor 296 toward the tissue being examined. Light reflected from the tissue surface passes back through the prism 297 to the sensor 296. The sensed returned light will be at a maximum when the beam from the beam generated by the sensor 296 is 90° incident to the tissue surface. The mechanism described above for moving a palpation tip 218 in three dimensions can thus adjust the tip orientation to provide palpation at 90° to the breast surface.

A motor 300 in each laser beam positioning enclosure 294 drives a lead screw 302 that engages an arcuate gear sector 304 to rotate each sensor 296 and prism 297 about the center of rotation of gear sector 304. The laser diode within sensor 296 generates a laser beam that produces a red dot on the tissue being examined. A conventional sensor 306 within each enclosure 294 counts rotation of the lead screw 302 and is calibrated to indicate the exact distance to the surface upon which the dot appears when the beam is at 90° to the surface. The system computer then can conventionally calculate a three dimensional image of the tissue surface from a number of these angle readings.

Lens assembly 286, in conjunction with a light sensor 308, a pre-focused sensor lens 310 and lenses 312 operate in the same manner as a camera automatic focusing systems to bring the tissue surface into sharp optical focus by rotating the lead screw 290 as necessary. A position sensor 313 counts rotation of the lead screw 290 to provide position information to the processor 17 or some other system such as a computer. As the optical locator 16 moves and focuses on the tissue, the palpation detector 14 is brought into contact with the tissue surface.

Extreme position sensors 314 are preferably provided to sense movement of the lens enclosure 284 to the ends of its desired range of movement and prevent damage which might be caused by movement outside the selected range. Sensors 314 may be conventional sensors, such as electro-optical or pressure switches, which can turn off motor 288.

Multi-dimensional Mapping

In operation, either of the locator 16 embodiments shown in FIGS. 5 and 15 can be conventionally programmed to map an entire breast and associated tissue step by step. The horizontal and vertical (X and Y) movements of the robot arm (carriage) 11 position the location device 16 at selected points across the tissue under investigation. The focusing mechanism within the motor housing 282 and the lens enclosure 284 continually focus the sensor 308 to provide the necessary Z direction alignment. The position sensor 313 will count the revolution of the motor 288 while the motor brings the lens assembly 286 to the point of focus to continuously provide lens position information.

Once the locator 16 has visited all desired points of the tissue and a calculation is made of the distance from every desired point, the processor 17 generates a multi-dimensional image (two or three dimensions) of the tissue under investigation.

For example, during palpation of a breast, the locator 16 verifies the location being palpated and can automatically compensate for breast movement as the patient breathes. In addition, a map of the breast is produced by a video camera 316 mounted with the locator 16 as shown in FIG. 14. Other types of mapping can be produced using the distance traveled by the palpation probe 92, the velocity of travel of the palpation probe 92, and the time of palpation at each contact point. For example, velocity data may be used, preferably in conjunction with the distance traveled and time data, to calculate the breast tissue density at each palpation point. Thus, the apparatus of this invention will provide an accurate map of the breast as well as detect tissue density anomalies, and provide the ability to accurately reexamine the breast from time to time to monitor any changes in breast density anomalies.

Sampling Devices

Figure 16:
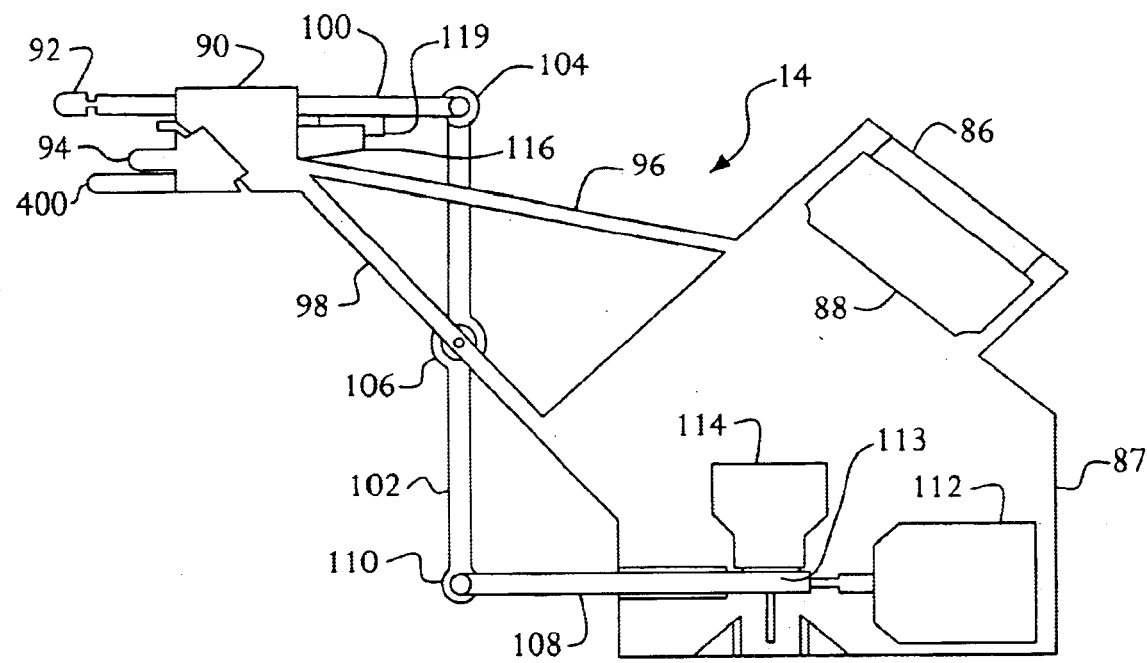
FIG. 16 illustrates a detection head and actuator having a sampling device according to the present invention.
Figure 17:
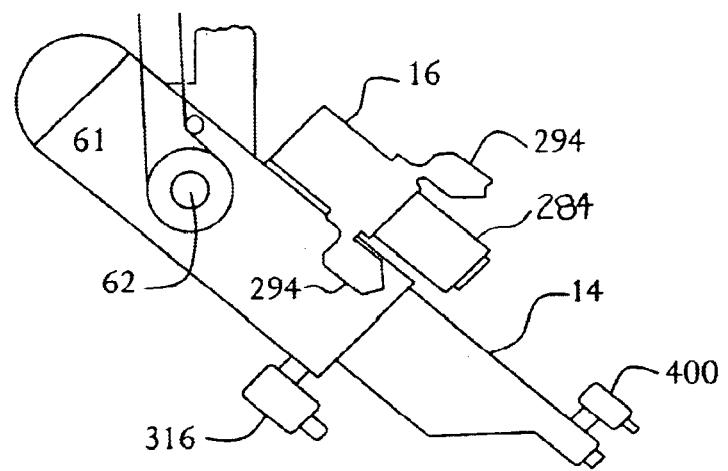
FIG. 17 illustrates an optical locating head and detection head having a sampling device mounted to a carriage according to the present invention.

In addition, referring to the alternative embodiments illustrated in FIGS. 16 and 17, a sampling device 400 is provided to further examine the identified regions of tissue density anomalies in order to determine the predetermined tissue characteristics and regions such as, but not limited to, skin, fat, muscle, and abnormal tissue such as cancer. The sampling device 400 is connected to a detector 14 that is in communication with the processor 17. The sampling device 400 may be an invasive or non-invasive device 402, such as but not limited to a needle, aspirator, coring device, ultrasound device, temperature device, electromagnetic sensing device, impedance measurement device, or some combination thereof The sampling device 400 is positioned by the processor 17 at predetermined locations of the tissue under investigation By means of three dimensional mapping produced from the tissue density data, the sampling devices may be more effectively employed to obtain additional data or even tissue samples from the tissue under investigation.

Figure 18A:
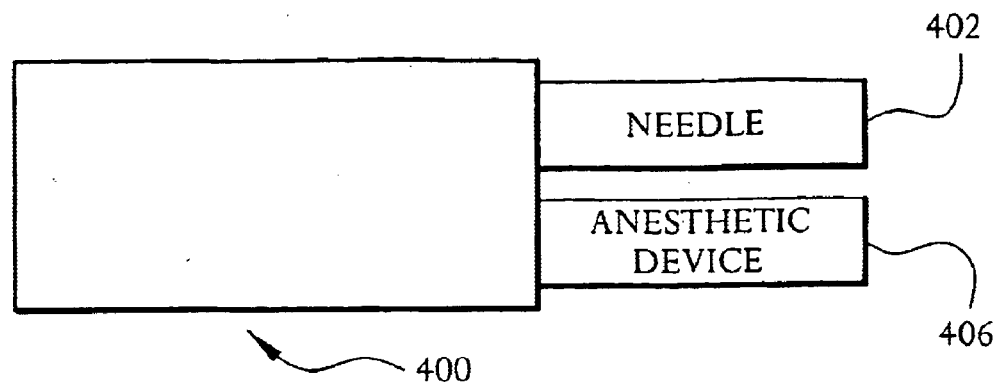
FIGS. 18a through 18c illustrate alternate embodiments of sampling devices according to the present invention.
Figure 18B:
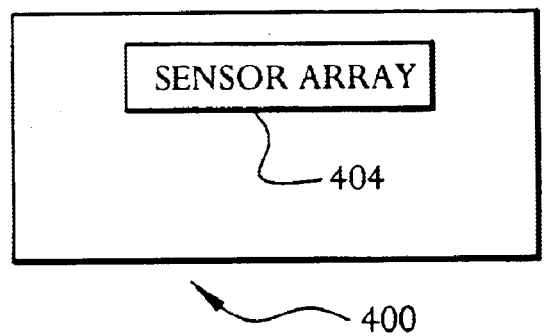
Figure 18C:
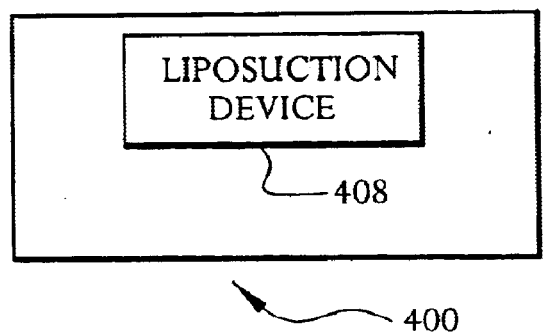

Other examples of sampling devices that may be incorporated with the invention are shown in FIGS. 18a–18c and include a biopsy needle and anesthetic delivery device 406, a multi-electrode sensor array 404 for examining detected tissue anomalies, a T-Scan 2000 manufactured by TransScan Research and Development Ltd. for detecting low-level electric currents and impedance to produce a real-time image of the electrical distribution within the breast, an ultrasound device, a temperature measuring device, or a liposuction device 408.

A Dynamic Color Imaging System

The present invention includes a color density imaging system capable of displaying images of tissue characteristics, in real time, detected and determined by the apparatus described above, or by other apparatus capable of providing tissue characteristics. The controller 17 of the apparatus 10 includes software that receives, stores and processes data detected by the apparatus, then transmits to a monitor color images of the tissue characteristics. The colors displayed in the image correspond to certain values of a predetermined tissue characteristic, or characteristics, for tissue displayed in the image. The data collected by the apparatus 10 can be in any standard bit format, depending upon the operating settings of the individual components of the apparatus 10.

The apparatus 10 collects four sets of data. The data is recorded into a designated file in the controller 17 and processed by the software to create the color image. The detector (or detection head) 14 collects data related to tissue characteristics. The locator (or location head) 16 collects data related to X and Y dimensions of the patient 68 relative to the location pattern 71 of the matrix board 66 and data related to the X and Y dimensions of the detection head 14 relative to tissue of the patient 68 and to the location pattern 71. The optical head (light source with focusing lenses or laser location device) of the locator 16 collects data related to the height (or Z dimension) of the detection head 14 relative to the tissue of the patient 68. The camera 134, 316 provides an initial image of the tissue of the patient 68 and collects data related to the X and Y dimensions of the tissue relative to the created image.

The software receives, processes and transmits for display an initial image of the tissue under investigation as provided by the camera 134, 316, dividing the image into predetermined portions. Associated with each portion of the image is data describing a first and a second coordinate of the tissue relative to the patient 68. The initial image is processed in one of any of a number of formats, depending on the operating system employed (e.g., a bit map:.bmp). The predetermined portions of the image could relate to individual pixels of the monitor or screen displaying the color image.

The software receives characteristic data of the tissue from the detection head 14 for each portion of the image. Data received from the location head 16 monitors the position of the detection head 14 relative to the tissue under investigation and associates the location of the detection head 14 (and characteristic data resulting therefrom) to each portion of the displayed image. Data collected from the optical head monitors the height (or Z dimension) of the detection head 14 relative to the tissue under investigation to associate the location of the detection head (and characteristic data resulting therefrom) with the Z dimension (or depth) of the tissue under investigation for use in recording characteristic data in three-dimensions and for creating (displaying) three-dimensional images of tissue characteristics.

The software associates (or assigns) a color, or shade thereof, to various incremental values of the characteristic data for each portion of the displayed image. The association of color to incremental values of characteristic data can be accomplished by first assigning a certain code to each incremental value of characteristic data. The software is programmed to then associate a particular color to every code. The color displayed for each portion of the image, therefore, results from the software determining a code for each portion of the image based upon the particular value of the characteristic data and then associating a color to the resultant code. Including code assignments in the color association process is especially useful when the characteristic data received and processed for color imaging includes data determined for each of a plurality of properties. Each property is assigned a set of codes and a certain code within the set is assigned to the property depending upon the incremental value determined for that property by the detection head 14. A resultant code (for each portion of the image) is then calculated based upon a formula that considers the certain code assigned for each property, and the number of properties included in the characteristic data. The formula may be weighted, giving greater consideration to one or more particular properties, or to particular codes within each property. The software then proceeds to associate a color to the resultant code for each portion of the image.

In one embodiment of the invention, the characteristic data includes just one property: tissue density. Tissue density is determined by software which processes data collected by the detection head 14 related to distance traveled by the palpation probe 218, velocity of travel of the palpation probe 218 and a time of palpation at each palpation probe contact point with tissue. However, the characteristic data could be any property, or a combination of properties selected from the group consisting of tissue density, tissue temperature, tissue color, tissue resistance, tissue conductivity, tissue impedance, tissue ultrasound results and tissue sampling results. In addition, the data collected by the detection head 14 to determine tissue density could also be characteristic data (i.e., any one or combination of properties related to palpation probe 218 information, such as distance traveled by the palpation probe 218, velocity of travel of the palpation probe 218 and a time of palpation at each contact point (for each portion of the image).

In another embodiment of the invention, a specific area of the tissue under investigation (defined by X and Y coordinates) has characteristic data determined, processed, recorded and displayed for each portion of the image and for each portion of the image for each of a plurality of levels (or layers in Z dimension). The optical head of the location device 16, in conjunction with the detection head 14, allow for the multiple level processing of characteristic data in three-dimensions. Due to the two-dimensional limitations of typical computer monitors or display screens, multiple color images are processed and displayed for a particular X and Y coordinate of tissue under investigation, one image for each level (or incremental Z coordinate value). The images relating to incremental levels (or layers) of tissue depth can be scrolled through, one by one, for the particular X and Y coordinates of tissue under investigation.

In another embodiment of the invention, secondary software processes and displays the multiple image layers, one over another in right sequential order, to create a virtal three-dimensional image for aparticular X and Y coordinate of the tissue under investigation. The three-dimensional image allows an analyst to easily and expeditiously determine the existence and location of tissue anomalies in three-dimensions.

In another embodiment of the invention, the virtual three-dimensional image for a particular X and Y coordinate of the tissue displays a color, for each portion of the image, that considers the value of the characteristic data for each level (or Z dimension) simultaneously displayed for the respective portion (X and Y coordinate) of the image. The software includes a formula that considers the value of the characteristic data for each level simultaneously displayed for each portion of the image. The formula can be weighted, giving greater consideration to the value of characteristic data of levels in closer proximity to the level displayed by the three-dimensional image.

A color image having uniform color throughout the image (i.e., uniform color from portion to portion over the image) represents tissue having similar, or nearly similar, characteristic data for the entire area of tissue displayed. A variation of color from portion to portion over the two or three-dimensional color image signifies that the characteristic data of tissue also vary from portion to portion over the tissue under investigation. For example, if the characteristic data is tissue density, and the palpation probe 218 of the detection head 14 collects data relating to a tissue abnormality (i.e., a high density mass) at a particular tissue location, the color of the corresponding tissue location on the image will vary relative to the color displayed at other portions of the image. The degree of color variation, from portion to portion over the image, will depend on the degree of density variation from portion to portion over the tissue under investigation.

Naturally, different areas of tissue may inherently have different characteristic data, and such would be displayed by the color image. For example, if the color image displays breast tissue and the characteristic data is tissue density, the nipple area of the breast would be displayed with color differing from that displayed for other breast areas.

In another embodiment of the invention, the software calculates, records and provides, on command, the size of tissue defined by a certain, predetermined characteristic value. These calculations of size can be in two or three dimensions. Associated with this calculation and recordation is the coordinate location information of the respective mass relative to the tissue. This information is stored for further, comparative analysis at subsequent tissue examinations. The two-dimensional and/or three dimensional color images are also stored (along with the location of the tissue displayed relative to the patient) for comparative analysis at subsequent examinations.

In another embodiment of the invention, the system processes recorded information related to characteristic data of tissue determined for selected first, second and third coordinates of tissue relative to a subject body and programmably compares the characteristic data with previously (i.e., at a previous examination) determined characteristic data related to the same first, second and third coordinates of tissue relative to the same subject body. The system displays an image of the selected first, second and third coordinates of the tissue under investigation, and color is assigned to each portion of the image based upon a formula that calculates any change, and degree thereof, in the characteristic data for that portion of the image. A pre-determined color is associated with certain incremental values of change in the characteristic data (i.e., change in characteristic data between selected examinations) for each portion of the image. The color image provides a quick and accurate means to determine the existence, location and degree of change, over time, in selected characteristic data for any three-dimensional region of tissue.

In another embodiment of the invention, the changes in the characteristic data between different examination events, calculated for each portion of the image, are directed to a difference, in absolute value, of the respective characteristic data. The changes calculated, however, could be directed to a first derivative analysis of the respective characteristic data compared, for each portion of the image. Or, the changes calculated could incorporate both, using a formula that considers both the change in absolute value between the characteristic value of two examination events and the first derivative analysis of the characteristic value, for each portion of the image.

In another embodiment of the invention, the formula is weighted, giving greater consideration to either the change in absolute value or the first derivative analysis. The formula, in one embodiment, is weighted depending on the specific portion of the image under investigation. For instance, the formula might heavily weigh the first derivative analysis for portions of the image displaying the perimeter of a suspect mass, and heavily weigh the change in absolute value for interior portions of the suspect mass and for tissue of otherwise normal characteristic value. In this scenario, the color image portraying change better details and more accurately displays a change in a suspect mass, over time, by focussing on the change in characteristic data relative to neighboring, normal tissue (through use of the first derivative analysis) for perimeter areas of the suspect mass, and by focussing on the change in absolute value for interior portions of the suspect mass and for tissue of otherwise normal characteristic value (through use of the change in absolute value) so that the image is not empty, or void, in those portions.

While certain specific relationships, materials and other parameters have been detailed in the above description of embodiments, these can be varied, where suitable, with similar results. In particular, application to assess and image other parts of the body is possible, such as, but not limited to, the face, abdomen, thighs, buttocks, etc. In these regions as well as the breast, the method and system of the present invention may be used for the imaging of subcutaneous fat. In addition, the present invention may assess, image, and track the cancerous state of skin lesions. Furthermore, all of the above could be applied to other mammals.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A method for imaging tissue characteristics, comprising the steps of:
   a. developing an image of tissue, the image divided into pre-determined portions and accompanied by data describing a first and a second coordinate of the tissue relative to a subject body for each portion of the image;
   b. receiving characteristic data of the tissue for each portion of the image, each portion of the image having a first and a second coordinate relative to the image;
   c. associating a color to the characteristic data for each portion of the image; and
   d. displaying the color for each portion of the image, whereby differing colors displayed over the image assist in determining the existence of tissue anomalies in the subject body.

2. The method of claim 1, wherein each portion of the image is a pixel.

3. The method of claim 1, wherein the characteristic data is density.

4. The method of claim 1, further including the step of calculating and recording a size for tissue of predetermined characteristic value.

5. The method of claim 1, wherein the image of tissue is received from a camera.

6. The method of claim 1, wherein the data describing the first and the second coordinate of the tissue relative to a subject body is received from a camera.

7. The method of claim 1, wherein the characteristic data of the tissue is received from a palpation device.

8. The method of claim 1, wherein a location head provides positional data associating the characteristic data detected by the palpation device with the portion of the image relating to the first and the second coordinate of the tissue detected.

9. The method of claim 1, wherein the characteristic data is selected from the group consisting of tissue density, temperature, color, resistance, conductivity, impedance, ultrasound and sampling information.

10. The method of claim 1, wherein the characteristic data is selected from the group consisting of a distance traveled by a palpation probe, a velocity of travel of the palpation probe and a time of palpation at each contact point.

11. The method of claim 1, further comprising the step of receiving characteristic data of the tissue for each portion of the image for each of a plurality of third coordinate values and data describing the respective third coordinate value of the tissue relative to the subject body for each portion of the image.

12. The method of claim 11, wherein multiple image layers can be displayed, each image layer corresponding to a different incremental third coordinate value of the tissue relative to the subject body, each respective portion of the multiple image layers having similar first and second coordinates of the tissue relative to the subject body.

13. The method of claim 12, wherein the multiple image layers are displayed simultaneously, one over another, to create a virtual, three-dimensional image, whereby locating, in three-dimensions, tissue anomalies within the subject body is possible through inspection of the three-dimensional color image.

14. The method of claim 13, wherein the color displayed for each portion of the three-dimensional image is selected based on a formula that considers the characteristic data of the tissue for each layer simultaneously displayed for that respective portion.

15. The method of claim 14, wherein the formula is weighted, giving greater consideration to the characteristic data of the tissue for layers in closer proximity to the layer displayed by the three-dimensional image.

16. The method of claim 11, further including the step of calculating and recording a three-dimensional size for tissue of pre-determined characteristic value.

17. A method for imaging tissue characteristics, comprising the steps of:
   a. developing an image of tissue, the image divided into pre-determined portions and accompanied by data describing a first and a second coordinate of the tissue relative to a subject body for each portion of the image;
   b. receiving characteristic data of the tissue for each portion of the image, each portion of the image having a first and a second coordinate relative to the image;
   c. associating a code to the characteristic data for each portion of the image;
   d. associating a color to each code; and
   e. displaying the color for each portion of the image, whereby differing colors displayed over the image assist in determining the existence of tissue anomalies.

18. The method of claim 17, wherein each portion of the image is a pixel.

19. The method of claim 17, further including the step of calculating and recording a size for tissue of pre-determined characteristic value.

20. The method of claim 17, wherein the characteristic data includes data determined for each of a plurality of properties.

21. The method of claim 20, wherein a different set of codes is assigned to each of the plurality of properties.

22. The method of claim 21, wherein associating a color to each code associates a color to a resultant code, the resultant code calculated based on a formula that considers each of the plurality of properties and a respective value of the data determined for each property.

23. The method of claim 22, wherein the formula provides a pre-determined weight for each property and for the respective value of the data determined for each property.

24. The method of claim 17, wherein the characteristic data is density.

25. The method of claim 17, wherein the characteristic data is selected from the group consisting of tissue density, temperature, color, resistance, conductivity, impedance, ultrasound and sampling information.

26. The method of claim 17, wherein the characteristic data is selected from the group consisting of a distance traveled by a palpation probe, a velocity of travel of the palpation probe and a time of palpation at each contact point.

27. The method of claim 17, further comprising the step of receiving characteristic data of the tissue for each portion of the image for each of a plurality of third coordinate values and data describing the respective third coordinate value of the tissue relative to the subject body for each portion of the image.

28. The method of claim 27, wherein multiple image layers can be displayed, each image layer corresponding to a different incremental third coordinate value of the tissue relative to the subject body, each respective portion of the multiple image layers having similar first and second coordinates of the tissue relative to the subject body.

29. The method of claim 28, wherein the multiple image layers are displayed simultaneously, one over another, to create a virtual, three-dimensional image, whereby locating, in three-dimensions, tissue anomalies within the subject body is possible through inspection of the three-dimensional color image.

30. The method of claim 29, wherein the color displayed for each portion of the three-dimensional image is selected based on a formula that considers the characteristic data of the tissue for each layer simultaneously displayed for that respective portion.

31. The method of claim 30, wherein the formula is weighted, giving greater consideration to the characteristic data of the tissue for layers in closer proximity to the layer displayed by the three-dimensional image.

32. The method of claim 27, further including the step of calculating and recording a three-dimensional size for tissue of pre-determined characteristic value.

33. A method for creating color images of tissue density, comprising the steps of:
   a. developing an image of tissue, the image divided into predetermined portions and accompanied by data describing a first and a second coordinate of the tissue relative to a subject body for each portion of the image;
   b. receiving a density value of the tissue for each portion of the image, each portion of the image having a first and a second coordinate relative to the image;
   c. associating a color to the density value for each portion of the image; and
   d. displaying the color for each portion of the image, whereby different colors displayed over the image relate to different densities of tissue and thereby assist in determining the existence of tissue anomalies.

34. A method for creating three-dimensional color images of tissue density, comprising the steps of:
   a. developing an image of tissue, the image divided into pre-determined portions and accompanied by data describing a first and a second coordinate of the tissue relative to a subject body for each portion of the image;
   b. receiving a density value of the tissue for each portion of the image, each portion of the image having a first and a second coordinate relative to the image;
   c. receiving a density value of the tissue for each portion of the image for each of a plurality of third coordinate values and data describing the respective third coordinate value of the tissue relative to the subject body for each portion of the image;
   d. assigning a color for each portion of the image, the color assignment based on a formula that considers the density value of the tissue for each respective third coordinate value; and
   e. displaying the color for each portion of the image, whereby different colors displayed over the image relate to different densities of tissue in three-dimensions, thereby assisting in determining the existence of tissue anomalies within the subject body.

35. The method of claim 34, wherein the formula is weighted, giving greater consideration to the density value of the tissue for third coordinate values in closer proximity to the third coordinate value displayed by the three-dimensional image.

36. The method of claim 34, further including the step of calculating and recording a three-dimensional size for tissue of pre-determined characteristic value.

37. A method for creating color images displaying tissue characteristics, comprising the steps of:
   a. developing an image of tissue, the image divided into pre-determined portions and accompanied by data describing a first and a second coordinate of the tissue relative to a subject body for each portion of the image;
   b. receiving characteristic data of the tissue for each portion of the image, wherein the characteristic data includes detected values for a plurality of properties;
   c. determining a resultant code for the characteristic data, wherein a set of codes is associated with each property, a certain code within the set is associated with the detected value of the respective property, and the resultant code is calculated using a formula that considers each detected value and each property;
   d. associating a color to each resultant code; and
   e. displaying the color for each portion of the image, whereby differing colors displayed over the image assist in determining the existence and location of tissue anomalies.

38. A method for creating three-dimensional color images displaying tissue characteristics, comprising the steps of:
   a. developing an image of tissue, the image divided into pre-determined portions and accompanied by data describing a first and a second coordinate of the tissue relative to a subject body for each portion of the image;
   b. receiving characteristic data of the tissue for each portion of the image and for each portion of the image for each of a plurality of levels, wherein the characteristic data includes detected values for a plurality of properties;
   c. determining a resultant code for the characteristic data for each portion of the image and for each portion of the image for each of a plurality of levels, wherein a set of codes is associated with each property, a certain code within the set is associated with the detected value of the respective property, and the resultant code is calculated using a formula that considers each detected value and each property;
   d. assigning a color for each portion of the image, the color assignment based on a weighted formula that considers the resultant code for each of the plurality of levels for the respective portion of the image, the weighted formula giving greater consideration to the resultant code for respective levels in closer proximity to the level in the image; and
   e. displaying the color for each portion of the image, whereby differing colors displayed over the image assist in determining the existence and location of tissue anomalies in three dimensions.

39. A method of displaying changes in tissue characteristics, over time, by color image, comprising the steps of:
   a. developing an image of tissue, the image divided into pre-determined portions and accompanied by data describing coordinates of the tissue relative to a subject body for each portion of the image;

b. receiving characteristic data of the tissue for each portion of the image for separate instances in time, each portion of the image having a first and a second coordinate relative to the image;

c. determining a value of a difference in the characteristic data of the tissue for each portion of the image for the separate instances in time;

d. associating a color to the value of the difference in the characteristic data for each portion of the image; and e. displaying the color for each portion of the image, whereby differing colors displayed over the image assist in determining the existence and location of changes in tissue characteristics over time for the subject body.

40. The method of claim 39, wherein determining the value of the difference in the characteristic data of the tissue for each portion of the image for the separate instances in time is based upon a formula that calculates the difference in the characteristic data for the separate instances in time, and degree thereof, for each portion of the image.

41. The method of claim 40, wherein associating a color to the value of the difference is based upon having a pre-determined color assigned to certain incremental values of difference in the characteristic data, whereby the color image provides a quick and accurate means to determine the existence, location and degree of difference, over time, in characteristic data of tissue for the subject body.

42. The method of claim 40, wherein the formula considers both a difference, in absolute value, of the characteristic data and a first derivative analysis of the characteristic data.

43. The method of claim 42, wherein the formula is weighted depending on the portion of the image, the formula giving greater weight to the first derivative analysis for portions of the image displaying a perimeter of a suspect mass and giving greater weight to the difference in absolute value of the characteristic data for interior portions of the suspect mass and for tissue of normal characteristic value.

44. The method of claim 39, wherein determining the value of the difference in the characteristic data relates to either determining a difference, in absolute value, of the characteristic data or to a first derivative analysis of the characteristic data.

45. A computer-readable medium that configures a computer system to perform a method for imaging tissue characteristics, the method comprising the steps of:

a. developing an image of tissue, the image divided into pre-determined portions and accompanied by data describing a first and a second coordinate of the tissue relative to a subject body for each portion of the image;

b. receiving characteristic data of the tissue for each portion of the image, each portion of the image having a first and a second coordinate relative to the image;

c. associating a color to the characteristic data for each portion of the image; and d. displaying the color for each portion of the image, whereby differing colors displayed over the image assist in determining the existence of tissue anomalies in the subject body.

46. A computer-readable medium that configures a computer system to perform a method for imaging tissue characteristics, the method comprising the steps of:

a. developing an image of tissue, the image divided into pre-determined portions and accompanied by data describing a first and a second coordinate of the tissue relative to a subject body for each portion of the image;

b. receiving characteristic data of the tissue for each portion of the image, each portion of the image having a first and a second coordinate relative to the image;

c. associating a code to the characteristic data for each portion of the image;

d. associating a color to each code; and e. displaying the color for each portion of the image, whereby differing colors displayed over the image assist in determining the existence of tissue anomalies.

47. A computer-readable medium that configures a computer system to perform a method for creating color images of tissue density, the method comprising the steps of:

a. developing an image of tissue, the image divided into pre-determined portions and accompanied by data describing a first and a second coordinate of the tissue relative to a subject body for each portion of the image;

b. receiving a density value of the tissue for each portion of the image, each portion of the image having a first and a second coordinate relative to the image;

c. associating a color to the density value for each portion of the image; and d. displaying the color for each portion of the image, whereby different colors displayed over the image relate to different densities of tissue and thereby assist in determining the existence of tissue anomalies.

48. A computer-readable medium that configures a computer system to perform a method for creating three-dimensional color images of tissue density, the method comprising the steps of:

a. developing an image of tissue, the image divided into pre-determined portions and accompanied by data describing a first and a second coordinate of the tissue relative to a subject body for each portion of the image;

b. receiving a density value of the tissue for each portion of the image, each portion of the image having a first and a second coordinate relative to the image;

c. receiving a density value of the tissue for each portion of the image for each of a plurality of third coordinate values and data describing the respective third coordinate value of the tissue relative to the subject body for each portion of the image;

d. assigning a color for each portion of the image, the color assignment based on a formula that considers the density value of the tissue for each respective third coordinate value; and e. displaying the color for each portion of the image, whereby different colors displayed over the image relate to different densities of tissue in three-dimensions, thereby assisting in determining the existence of tissue anomalies within the subject body.

49. A computer-readable medium that configures a computer system to perform a method for creating color images displaying tissue characteristics, the method comprising the steps of:

a. developing an image of tissue, the image divided into pre-determined portions and accompanied by data describing a first and a second coordinate of the tissue relative to a subject body for each portion of the image;

b. receiving characteristic data of the tissue for each portion of the image, wherein the characteristic data includes detected values for a plurality of properties;

c. determining a resultant code for the characteristic data, wherein a set of codes is associated with each property, a certain code within the set is associated with the detected value of the respective property, and the resultant code is calculated using a formula that considers each detected value and each property;

d. associating a color to each resultant code; and e. displaying the color for each portion of the image, whereby differing colors displayed over the image assist in determining the existence and location of tissue anomalies.

50. A computer-readable medium that configures a computer system to perform a method for creating three-dimensional color images displaying tissue characteristics, the method comprising the steps of:

a. developing an image of tissue, the image divided into pre-determined portions and accompanied by data describing a first and a second coordinate of the tissue relative to a subject body for each portion of the image;

b. receiving characteristic data of the tissue for each portion of the image and for each portion of the image for each of a plurality of levels, wherein the characteristic data includes detected values for a plurality of properties;

c. determining a resultant code for the characteristic data for each portion of the image and for each portion of the image for each of a plurality of levels, wherein a set of codes is associated with each property, a certain code within the set is associated with the detected value of the respective property, and the resultant code is calculated using a formula that considers each detected value and each property;

d. assigning a color for each portion of the image, the color assignment based on a weighted formula that considers the resultant code for each of the plurality of levels for the respective portion of the image, the weighted formula giving greater consideration to the resultant code for respective levels in closer proximity to the level in the image; and e. displaying the color for each portion of the image, whereby differing colors displayed over the image assist in determining the existence and location of tissue anomalies in three dimensions.

51. A computer-readable medium that configures a computer system to perform a method of displaying changes in tissue characteristics, over time, by color image, the method comprising the steps of:

a. developing an image of tissue, the image divided into pre-determined portions and accompanied by data describing coordinates of the tissue relative to a subject body for each portion of the image;

b. receiving characteristic data of the tissue for each portion of the image for separate instances in time, each portion of the image having a first and a second coordinate relative to the image;

c. determining a value of a difference in the characteristic data of the tissue for each portion of the image for the separate instances in time;

d. associating a color to the value of the difference in the characteristic data for each portion of the image; and e. displaying the color for each portion of the image, whereby differing colors displayed over the image assist in determining the existence and location of changes in tissue characteristics over time for the subject body.

52. A computer-readable medium that stores a program for imaging tissue characteristics, the program comprising:

a. means for developing an image of tissue, the image divided into pre-determined portions and accompanied by data describing a first and a second coordinate of the tissue relative to a subject body for each portion of the image;

b. means for receiving characteristic data of the tissue for each portion of the image, each portion of the image having a first and a second coordinate relative to the image;

c. means for associating a color to the characteristic data for each portion of the image; and d. means for displaying the color for each portion of the image, whereby differing colors displayed over the image assist in determining the existence of tissue anomalies in the subject body.

53. A computer-readable medium that stores a program for imaging tissue characteristics, the program comprising:

a. means for developing an image of tissue, the image divided into pre-determined portions and accompanied by data describing a first and a second coordinate of the tissue relative to a subject body for each portion of the image;

b. means for receiving characteristic data of the tissue for each portion of the image, each portion of the image having a first and a second coordinate relative to the image;

c. means for associating a code to the characteristic data for each portion of the image;

d. means for associating a color to each code; and e. means for displaying the color for each portion of the image, whereby differing colors displayed over the image assist in determining the existence of tissue anomalies.

54. A computer-readable medium that stores a program for creating color images of tissue density, the program comprising:

a. means for developing an image of tissue, the image divided into pre-determined portions and accompanied by data describing a first and a second coordinate of the tissue relative to a subject body for each portion of the image;

b. means for receiving a density value of the tissue for each portion of the image, each portion of the image having a first and a second coordinate relative to the image;

c. means for associating a color to the density value for each portion of the image; and d. means for displaying the color for each portion of the image, whereby different colors displayed over the image relate to different densities of tissue and thereby assist in determining the existence of tissue anomalies.

55. A computer-readable medium that stores a program for creating three-dimensional color images of tissue density, the program comprising:

a. means for developing an image of tissue, the image divided into pre-determined portions and accompanied by data describing a first and a second coordinate of the tissue relative to a subject body for each portion of the image;

b. means for receiving a density value of the tissue for each portion of the image, each portion of the image having a first and a second coordinate relative to the image;

c. means for receiving a density value of the tissue for each portion of the image for each of a plurality of third coordinate values and data describing the respective third coordinate value of the tissue relative to the subject body for each portion of the image;

d. means for assigning a color for each portion of the image, the color assignment based on a formula that considers the density value of the tissue for each respective third coordinate value; and e. means for displaying the color for each portion of the image, whereby different colors displayed over the image relate to different densities of tissue in three-dimensions, thereby assisting in determining the existence of tissue anomalies within the subject body.

56. A computer-readable medium that stores a program for creating color images displaying tissue characteristics, the program comprising:

a. means for developing an image of tissue, the image divided into pre-determined portions and accompanied by data describing a first and a second coordinate of the tissue relative to a subject body for each portion of the image;

b. means for receiving characteristic data of the tissue for each portion of the image, wherein the characteristic data includes detected values for a plurality of properties;

c. means for determining a resultant code for the characteristic data, wherein a set of codes is associated with each property, a certain code within the set is associated with the detected value of the respective property, and the resultant code is calculated using a formula that considers each detected value and each property;

d. means for associating a color to each resultant code; and e. means for displaying the color for each portion of the image, whereby differing colors displayed over the image assist in determining the existence and location of tissue anomalies.

57. A computer-readable medium that stores a program for creating three-dimensional color images displaying tissue characteristics, the program comprising:

a. means for developing an image of tissue, the image divided into pre-determined portions and accompanied by data describing a first and a second coordinate of the tissue relative to a subject body for each portion of the image;

b. means for receiving characteristic data of the tissue for each portion of the image and for each portion of the image for each of a plurality of levels, wherein the characteristic data includes detected values for a plurality of properties;

c. means for determining a resultant code for the characteristic data for each portion of the image and for each portion of the image for each of a plurality of levels, wherein a set of codes is associated with each property, a certain code within the set is associated with the detected value of the respective property, and the resultant code is calculated using a formula that considers each detected value and each property;

d. means for assigning a color for each portion of the image, the color assignment based on a weighted formula that considers the resultant code for each of the plurality of levels for the respective portion of the image, the weighted formula giving greater consideration to the resultant code for respective levels in closer proximity to the level in the image; and e. means for displaying the color for each portion of the image, whereby differing colors displayed over the image assist in determining the existence and location of tissue anomalies in three dimensions.

58. A computer-readable medium that stores a program for displaying changes in tissue characteristics, over time, by color image, the program comprising:

a. means for developing an image of tissue, the image divided into pre-determined portions and accompanied by data describing coordinates of the tissue relative to a subject body for each portion of the image;

b. means for receiving characteristic data of the tissue for each portion of the image for separate instances in time, each portion of the image having a first and a second coordinate relative to the image;

c. means for determining a value of a difference in the characteristic data of the tissue for each portion of the image for the separate instances in time;

d. means for associating a color to the value of the difference in the characteristic data for each portion of the image; and e. means for displaying the color for each portion of the image, whereby differing colors displayed over the image assist in determining the existence and location of changes in tissue characteristics over time for the subject body.

* * * * *